United States Patent [19]

Chang

[11] Patent Number: 5,752,966
[45] Date of Patent: May 19, 1998

[54] EXOVASCULAR ANASTOMOTIC DEVICE

[76] Inventor: David W. Chang, 10 Parkway Rd., Apt. #6, Brookline, Mass. 02146

[21] Appl. No.: 814,740

[22] Filed: Mar. 7, 1997

(Under 37 CFR 1.47)

[51] Int. Cl.⁶ .................................................. A61B 17/04
[52] U.S. Cl. ................................. 606/151; 606/153
[58] Field of Search .......................... 606/139, 151, 606/153

[56] References Cited

U.S. PATENT DOCUMENTS

| | | | |
|---|---|---|---|
| 1,756,670 | 4/1930 | Treat | 606/151 |
| 3,577,601 | 5/1971 | Mariani | 606/151 |
| 4,470,415 | 9/1984 | Wozniak | 128/334 R |
| 4,622,970 | 11/1986 | Wozniak | 128/334 R |
| 4,624,255 | 11/1986 | Schenck et al. | 128/334 R |
| 4,693,249 | 9/1987 | Schenck et al. | 128/334 R |
| 4,917,087 | 4/1990 | Walsh et al. | 606/153 |
| 4,930,674 | 6/1990 | Barak | 227/179 |
| 4,950,284 | 8/1990 | Green et al. | 606/151 |
| 4,955,864 | 9/1990 | Hajdach | 606/151 |
| 5,203,786 | 4/1993 | Vernick | 606/151 |
| 5,211,658 | 5/1993 | Clouse | 623/1 |
| 5,234,447 | 8/1993 | Kaster et al. | 606/153 |
| 5,397,345 | 3/1995 | Lazarus | 623/1 |
| 5,456,712 | 10/1995 | Maginot | 623/1 |
| 5,486,187 | 1/1996 | Schenck | 606/153 |
| 5,549,122 | 8/1996 | Detweilwer | 128/898 |
| 5,562,724 | 10/1996 | Vorwerk et al. | 623/1 |
| 5,562,726 | 10/1996 | Chuter | 623/1 |
| 5,571,173 | 11/1996 | Parodi | 623/1 |

*Primary Examiner*—Gary Jackson
*Attorney, Agent, or Firm*—Nutter, McClennen & Fish, LLP

[57] ABSTRACT

An anastomotic device includes a flexible member, formable into a loop and a plurality of tissue penetrating anchoring elements slidably mounted on the flexible member. The tissue penetrating anchoring elements extend generally towards a center of the loop formed by the flexible member. The device is adapted for anastomosing vessel segments or a vessel and a graft. In a further embodiment, an exovascular anastomotic device is suitable for end-to-side anastomoses and it includes an anastomotic ring and a harness assembly.

22 Claims, 6 Drawing Sheets

5,752,966

EXOVASCULAR ANASTOMOTIC DEVICE

CROSS REFERENCE TO RELATED APPLICATIONS

Not Applicable.

STATEMENT REGARDING FEDERALLY SPONSORED RESEARCH

Not Applicable.

FIELD OF THE INVENTION

The present invention relates to devices useful with surgical anastomoses and more particularly to a sutureless anastomotic device.

BACKGROUND OF THE INVENTION

The joining of one hollow or tubular organ to another in a patient, known as is anastomosis, is a common surgical procedure. Blood vessels serve as an example of such organs for which anastomoses may be required. For example, a sharp foreign object or severe trauma can sever a blood vessel, requiring an anastomotic procedure to restore patency of the vessel. If a vessel is occluded or otherwise diseased, a bypass procedure may include replacing the occluded section with a portion of a vessel from another part of the body. Also, if a portion of a vessel is diseased or damaged, a synthetic graft, or prosthesis, may be introduced to replace that portion of the vessel.

Anastomoses procedures have been traditionally effected by using sutures to join the vessels and/or grafts. It will be appreciated by one of ordinary skill in the art that there are significant disadvantages associated with suturing vessels. For example, a high level of skill is required to properly join the vessels and/or grafts. The suturing of vessels and/or grafts is, moreover, a procedure that is quite time consuming. To anastomose a blood vessel having a diameter in the range of about five to twenty-five millimeters, approximately twenty to thirty well placed stitches must be placed about the circumference of the vessel, requiring at least fifteen minutes under optimal conditions.

The suturing process is further complicated by friable and rigid, calcified vessels increasing the time required for the procedure. As is known to one of ordinary skill in the art, longer operative times are associated with a greater likelihood of heart attack and infection. Moreover, any improper suturing can result in serious medical consequences, including hemorrhaging and infection.

Anastomosis of living vessels requires the vessel layers to be positioned properly with respect to each other. As shown in FIG. 1, a vessel, such as a human artery 10 has an inner layer (intima) 12, a middle layer (media) 14, and an outer layer (adventitia) 16.

To anastomose a vessel or graft, the sutures must be precisely placed using a curved needle to pierce the vessel first from the outside, and then from the inside back to the outside of the vessel. As noted above, such a suturing process is time consuming and demands a high level of precision. Time is especially critical in procedures that require repair of a major artery.

Suture-based anastomoses have inherent limitations because the mechanical strength of the sutures join the graft and the vessel. Suturing can be especially difficult in cases where a vessel is so diseased or so severely damaged that there is only a limited amount of healthy tissue to which the sutures can be anchored. The brittleness of some diseased vessels can render them less amenable to suture-based anastomotic procedures.

There are inherent advantages to minimally invasive laparoscopic procedures. However, the limited degree of freedom afforded by the closed surgical environment compounds the difficulties associated with suture-based anastomotic procedures.

Because suture-based anastomotic procedures suffer from the drawbacks noted above, attempts have been made to develop sutureless anastomotic devices. See, for example, U.S. Pat. Nos. 4,470,415, 4,917,087, 4,930,674, and 5,486,187. However, the complexity of such devices and/or their lack of ease of use have limited their clinical acceptance. There is thus a need for a sutureless anastomotic device that can be easily 10 and effectively used in a variety of anastomotic procedures.

SUMMARY OF THE INVENTION

The present invention provides a sutureless anastomotic device useful in sutureless anastomotic procedures. In one embodiment the anastomotic device is an exovascular anastomotic device. Although the invention is primarily described and illustrated as an exovascular anastomotic device, it is understood that it can be used for other anastomoses procedures such as gastro-intestinal anastomoses.

The device, in its initial configuration, is an elongate flexible member having first and second ends. One or more anchoring elements are disposed on the flexible member.

The anchoring elements preferably are each in the form of a tubular body having an axial passageway formed therein. One surface of the anchoring element has formed thereon at least one tissue-penetrating projection. The anchoring elements are preferably slidably mounted, through the axial passageway, upon the flexible member. Optimally, one or more spacer elements may be disposed on the flexible member between each, or selected, adjacent anchoring members to control the positioning of the anchoring members.

The flexible member is formable into a loop of an adjustable diameter. In one embodiment, one of the first or second ends of the flexible member includes a locking mechanism having an opening formed therein. In operation, the other of the first or second ends of the flexible member is threaded through the opening of the locking mechanism so that the flexible member assumes the shape of a loop. In this loop configuration, the anchoring elements are circumferentially oriented with the tissue-penetrating projections being inwardly directed, either radially inward or at a selected angle to the radius. Preferably, the anchoring elements are slidably mounted on the loop so that before installation of the device in an anastomotic procedure they can be positioned as needed; once the device is initially placed on a vessel the anchoring elements are stationary.

Surface features are preferably formed on at least one surface of the flexible member. These surface features interact with a complementary surface feature or other structure formed in the opening of the locking mechanism so that the end inserted into the locking mechanism can only be moved in one direction with respect to the locking mechanism. Preferably, this unidirectional movement enables the loop to be adjusted only in a manner to decrease its diameter.

In one embodiment, the anastomotic device is used by forming the flexible member into a loop that is circumscribed about an end of a first vessel segment. The end of the first vessel segment is then overlapped with an end of a second vessel segment. An initial adjustment to the diameter of the loop is made to cause the tissue-penetrating projections to penetrate the vessels. Thereafter, the flexible member is moved with respect to the anchoring elements (which remain stationary) to reduce the size of the loop until it is properly dimensioned about the vessels to anastomose the first and second vessel segments. An intravascular obturator (such as an obturator balloon) may be positioned within the vessel to assist in the anastomotic procedure.

In another embodiment, the anastomotic device of the invention can be used for an end-to-side anastomosis. In this embodiment, the device includes an anastomotic ring and a harness assembly having a harness ring coupled to at least one locking band. The anastomotic ring optionally includes at least one filamentary member fixedly secured to the anastomotic ring.

An end-to-side anastomosis can be conducted by placing a vessel or graft within the harness ring and then the anastomotic ring, and everting an end of the vessel or graft segment over the anastomotic ring. A receiving vessel is cut to form a substantially round hole, the opening of which tapers inwardly from the adventitia to the intima. The everted end of the vessel or graft is placed into the complementary hole formed in the receiving vessel and the harness ring is urged toward the anastomotic ring by cinching the locking band to the receiving vessel. The harness ring retains the everted end of the graft and anastomotic ring in the hole in the receiving vessel. The filamentary member(s) can secure the anastomotic ring to the harness assembly.

BRIEF DESCRIPTION OF THE DRAWINGS

The invention will be more fully understood from the following detailed description taken in conjunction with the following drawings, in which.

DETAILED DESCRIPTION OF THE INVENTION

Figure 1:
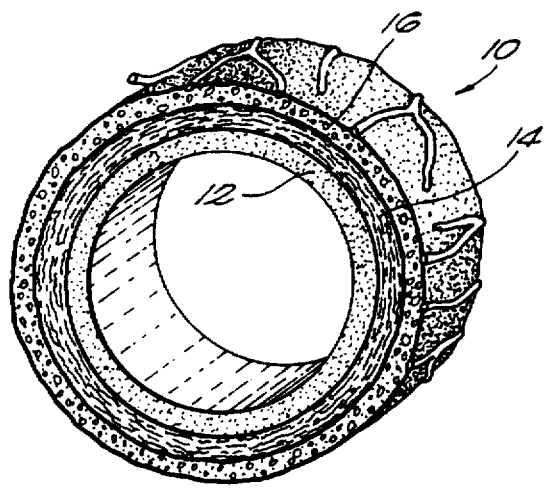
FIG. 1 is a prior art perspective view of an artery.

The drawings are understood to be illustrative of the concepts disclosed herein to facilitate comprehension of the invention. Further, the drawings are not to scale, and the scope of the invention is not to be limited to the particular embodiments shown and described herein.

Referring to FIGS. 2–8, a sutureless anastomotic device 100 includes a flexible member 102 having a first end 104 and a second end 106. A locking mechanism 108, or similar device, enables the formation of a closable loop and is secured to the first end 104 of the flexible member 102. The second end 106 is threaded through an opening 109 in the locking mechanism to form a loop. Anchoring elements 110 are slidably mounted on the flexible member 102. The anchoring elements 110 are preferably in the form of a tubular body 111 defining an axial passageway 112 therein. The anchoring elements 110 each include a first surface 114 having formed thereon a tissue-penetrating projection 116. In an exemplary embodiment, one or more spacer elements 118 can be disposed on the flexible member 102 between adjacent anchoring elements 110 to control the positioning and/or spacing of the anchoring elements.

It is understood that various alternative structures may be used as an alternative to locking mechanism 108. Suitable structures must allow the formation of a loop, having an adjustable diameter, from an initially elongate member. For example, the locking mechanism can include a screw element, advancement of which moves one end of the flexible member relative to the other end of the flexible member to reduce the diameter of the loop.

Each of the tissue-penetrating protrusions 116 include a first end 119 coupled to the tubular body, a generally pointed second end 120, and an intermediate portion 122. In an exemplary embodiment, the intermediate portion 122 has an annular cross section defining a substantially constant diameter along the length thereof. The tissue-penetrating protrusion 116 has a length in the range of about 0.1 to 5 millimeters, and preferably is about one millimeter. The diameter of protrusion 116 at the intermediate portion 122 is in the range of about 0.01 to 0.3 millimeters, and preferably about 0.1 millimeters. Other geometries for the tissue-penetrating protrusions 116 are also possible, such as conical and flattened, for example.

The anchoring elements 110 are formed from biocompatible materials having good mechanical properties. Exemplary materials include stainless steel, titanium, titanium alloys, metals, ceramics, and suitably rigid, biocompatible polymers. The device 100 is shown having six anchoring members 110, each having one tissue-penetrating protrusion 116. However, it is understood that a greater or lesser number of anchoring members 110 may be used, and that a member 110 may have more than one protrusion 116 (FIG. 7C). In a further embodiment, the second end 120 of the protrusions includes one or more barbs 123 (FIG. 7B) for securing the protrusions in tissue. Further, the protrusions 116 can extend from the tubular body 111 at any point on the first surface 114.

In an exemplary embodiment, the anchoring elements 110 are freely movable with respect to the flexible member 102 before protrusions 116 are embedded in tissue. The flexible member 102 is of sufficient width so as to provide lateral stability for the tissue-penetrating protrusions 116. Generally, the width of flexible member 102 ranges from about 1.5 millimeters to 2 centimeters, and more preferably from about 3 to 4 millimeters. The tissue-penetrating protrusions 116 should generally be oriented to form an acute angle with respect to a radial center point of the loop (FIG. 7B). This angle is generally in the range of about five to eighty degrees, and more preferably is about thirty degrees. The optimal angle for the protrusions 116 is determined by the amount of deformation that occurs as the protrusions penetrate tissue. More specifically, the more rigid the protrusions 116, the more the protrusions can be angled with respect to the radial centerpoint of the loop. In another embodiment, the protrusions 116 are directed to the radial centerpoint of the loop formed by the flexible member.

Figure 2:
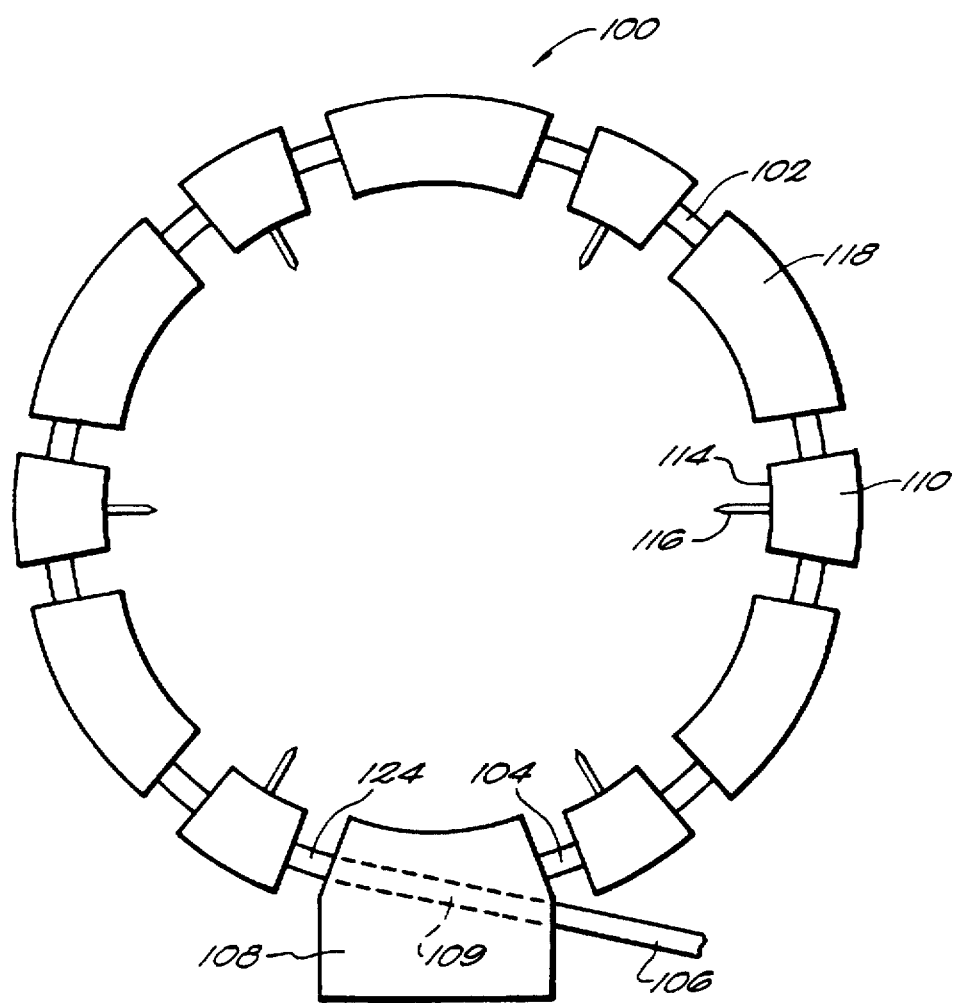
FIG. 2 is a side view of an exovascular anastomotic device in accordance with the present invention shown in an unengaged position.
Figure 3:
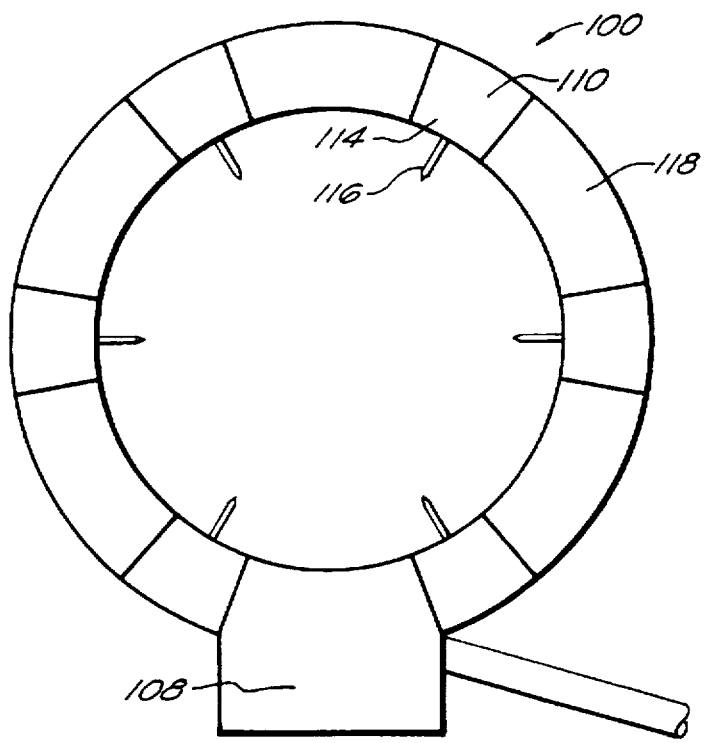
FIG. 3 is a side view of the anastomotic device of FIG. 2 shown in an engaged position.
Figure 4:
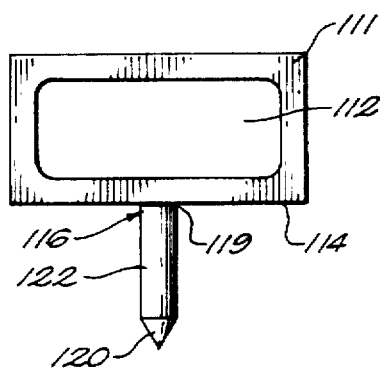
FIG. 4 is a side view of an anchoring element forming a portion of the anastomotic device of FIG. 2.
Figure 5:
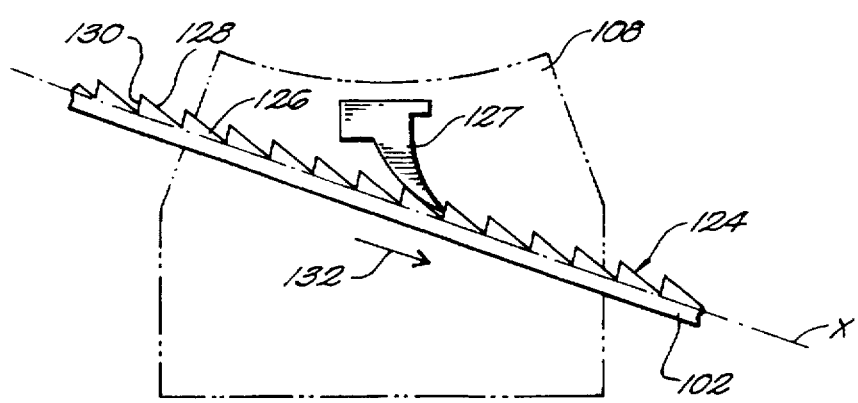
FIG. 5 is a enlarged sectional view of a portion of the locking mechanism and the flexible member, forming a portion of the anastomotic device of FIG. 2.

As illustrated in FIGS. 2 and 5, the flexible member 102 defines a first surface 124 having a plurality of surface features 126, which in an exemplary embodiment are spaced teeth. The surface features 126 can be disposed on the first surface 124 or an opposing surface of the flexible member 102, i.e., inward or outward with respect to the loop. The opening 109 in the locking mechanism 108 may include a structure such as a surface feature in the form of an arm 127, or a similar member, that is engageable with a respective one or more of the teeth 126 associated with the flexible member 102. In a preferred embodiment, each of the teeth 126 includes a sloped surface 128 defining an acute angle with respect to the longitudinal axis X of the flexible member and an engagement surface 130 extending generally perpendicular to the longitudinal axis X. It will be appreciated by one of ordinary skill in the art that the size of the teeth 126 may vary substantially. In an exemplary embodiment, the sloped surface 128 is about 0.3 millimeters in length and the engagement surface 130 is about 0.1 millimeters in height. The arm 127 is biased towards the flexible member 102 and contacts the engagement surface 130 of the respective tooth. As the flexible member 102 is moved in a first direction, indicated by arrow 132, the arm 127 elastically deforms as it slides up the sloped surface 128 and then returns to its original position as it reaches an adjacent engagement surface. The arm 127 operates in conjunction with the engagement surface 130 to prevent movement of the flexible member 102 in a direction opposite of the first direction 132. Thus, the surface features of the locking mechanism and the flexible member permit unidirectional movement of the flexible member with respect to the locking mechanism 108 to allow only a reduction in the size of the loop.

The flexible member 102 can be made from a variety of suitably flexible materials including biocompatible polymers. Exemplary materials include nylon polymers. The flexible member 102 can be formed from inelastic or moderately elastic materials known to one of ordinary skill in the art. Moderately elastic flexible members are useful as they expand in response to a pulse of a fluid through a vessel. In a further embodiment useful in gastrointestinal applications, the device is formed from biodegradable polymers, such as polyglyconate, so that the device need not be surgically removed after healing has taken place. Commercially available examples of such materials include POLYSORB and MAXON.

Figure 6:
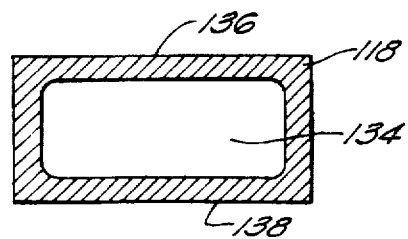
FIG. 6 is a sectional view of a spacer element forming a portion of the anastomotic device of FIG. 2.

As shown in FIG. 6, the optional spacer elements 118 preferably are tubular in shape, defining an aperture 134 through which the flexible member 102 may pass. Each of the spacer elements 118 includes an outer surface 136 and an inner surface 138 (as configured on the loop), wherein the inner surface is about the same distance from the flexible member 102 as the surface 114 of the anchoring elements 114. In one embodiment, one or more spacer elements 118 are located between adjacent tissue-penetrating protrusions 116 so that the anchoring elements are generally equally spaced about the loop as the size of the loop is reduced. However, it is understood that the anchoring elements need not necessarily be equally spaced. The spacer elements 118 preferably have sufficient flexibility or other physical characteristics (e.g., geometry) to enable then to conform to the curvature of the loop.

The dimensions of the spacer element can vary depending upon the requirements of a given application. The thickness (or height) of the spacer elements should be 10 consistent with the thickness of the tubular body portion of anchoring elements 114 to form a substantially continuous contact surface with a vessel or a graft. Typically, the thickness is in the range of about 0.02 to 0.2 millimeters. The width of the spacer elements 118 is in the range of about one to twenty millimeters, and preferably, is about the same width as the anchoring elements. The length of spacer elements 118 is in the range of about one half to about twice the length of the anchor elements, and it is understood that the spacer elements can be longitudinally compressible.

In one embodiment, the spacer elements can have a longitudinal slit along the length thereof so that one or more selected spacer elements can be removed or added to 20 the flexible member 102. In addition, a series of spacer elements 118 of the same or differing lengths can be disposed between adjacent anchor elements 110 to provide a desired spacing of the anchoring elements (FIG. 7C). One or more selected spacer elements can be removed or added to adjust the minimum diameter of the loop. In another embodiment, the spacer elements are formed from a material that can be cut with relative ease so that one or more selected spacer elements can removed from the loop.

One of ordinary skill in the art will appreciate that the spacer elements can be made from a variety of biocompatible materials, including metals, polymers and ceramics. Polymeric materials are preferred for most applications, and suitable exemplary polymers include polytetrafluoroethylene (PTFE) and other polymers known to those of ordinary skill in the art.

Figure 7:
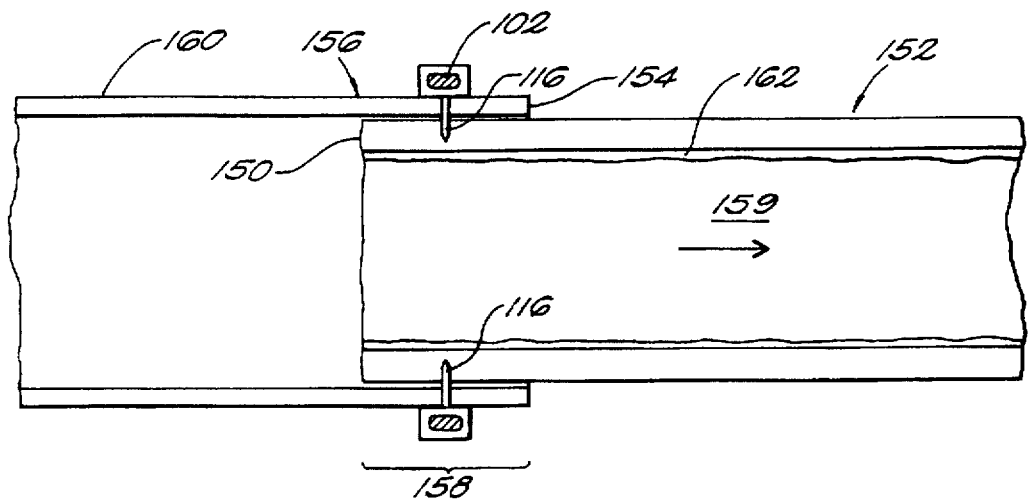
FIG. 7 is a cross sectional view of the anastomotic device of FIG. 2 disposed on a vessel.
Figure 7A:
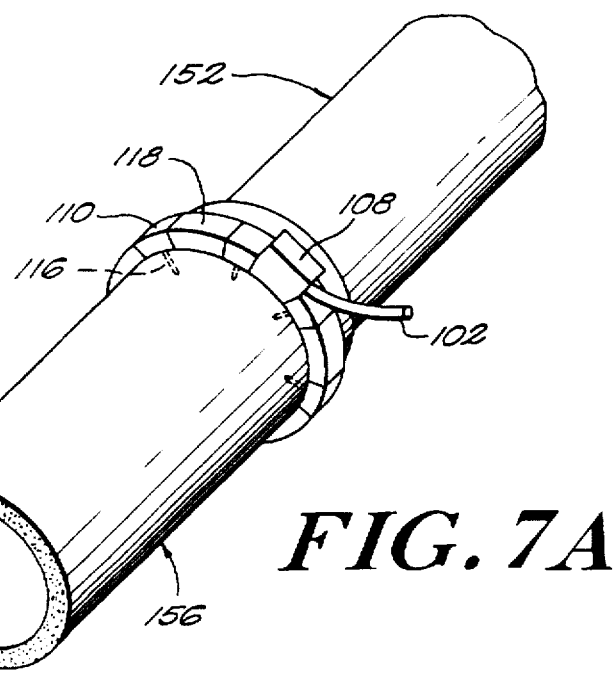
FIG. 7A is a perspective view of the anastomotic device of FIG. 7.
Figure 7B:
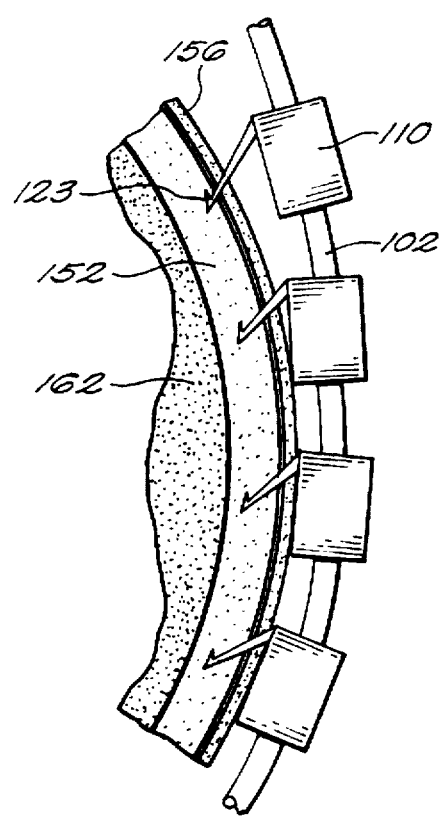
FIG. 7B is an enlarged cross sectional view of an alternative embodiment of the anastomotic device of FIG. 7.
Figure 7C:
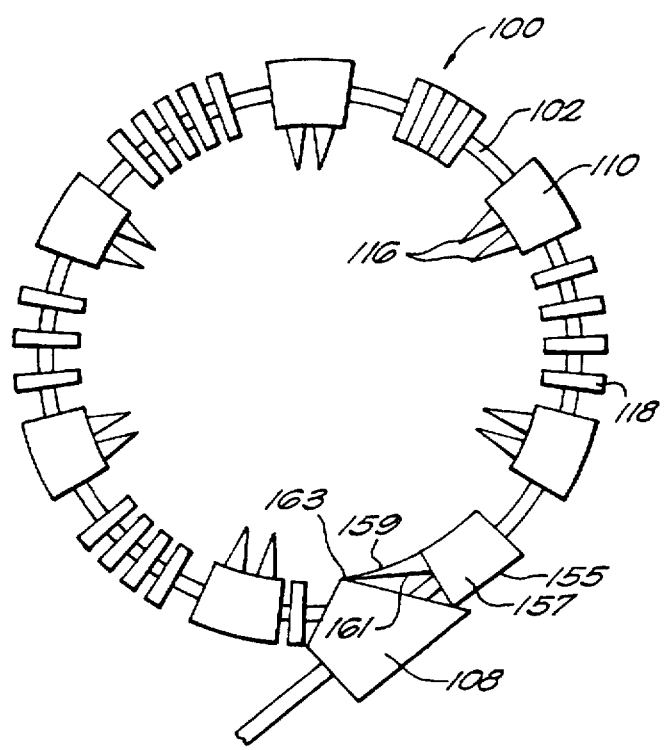
FIG. 7C is a side view of a further embodiment of the anastomotic device of FIG.7.

FIGS. 7 and 7A illustrate the use of a sutureless anastomotic device 100 according to the present invention in a distal anastomosis of an end 150 of a native blood vessel 152 and an end 154 of a graft 156. As indicated by arrow 159, the blood flow is in the direction from the graft 156 to the vessel 152. To effect this procedure, the end 154 of the graft is moved toward the device 100 so that the device, in the form of a loop, surrounds the graft 156. The end 150 of the vessel 152 is inserted within the end 154 of the graft so that portions of the vessel and the graft overlap at an overlap area 158. The flexible member 102 of the device is moved with respect to the locking mechanism (and the anchoring members) to decrease the size of the loop. As the loop contracts, the tissue-penetrating protrusions 116 penetrate the graft 156 and then the vessel 152. Contemporaneously, the spacer elements 118 slide with respect to the flexible member 102 so that surfaces 114, 138 of the anchoring elements and the spacer elements attain circumscribed engagement with an exterior surface 160 of the graft. As noted above, the anchoring elements 110 are freely slidable upon the flexible member 102. Once protrusions 116 penetrate tissue, however, anchoring elements 110 are stationary with respect to flexible member 102.

Upon initial penetration of the surface of the graft 156, the tissue-penetrating protrusions 116 are urged radially inward by the flexible member 102, without circumferential movement, as the loop diameter is further decreased. If the protrusions 116 are angled with respect to a radial centerpoint of the loop, tangential and radial force vectors are applied to the protrusions as the loop size decreases. The spacer elements 118 and the anchor elements provide substantially continuous contact with and substantially constant pressure on the graft outer surface 160 to prevent gaps that could result in leakage of blood between the artery 152 and the graft 152. The device is of sufficient flexibility so as to conform to any irregularities in the outer surface of the vessel.

The diameter of the loop is decreased by moving the flexible member 102 with respect to the locking mechanism 108 and the anchoring elements. One of ordinary skill in the art will appreciate that a variety of suitable applicator devices can be used. In one example, a suitable applicator gun (not shown) includes a head portion, a manual actuator mechanism, and a handle. In operation, the head portion abuts the locking mechanism 108 and the actuator mechanism engages the surface features 124 of the flexible member 102 for longitudinally displacing the flexible member with respect to the locking mechanism. A user, such as a surgeon, activates the actuator mechanism to manipulate the loop to a desired size.

In another embodiment, shown in FIG. 7C, the anastomotic device 100 can include one or more crimping elements 155 movably disposed on the flexible member 102. Such crimping members can be useful to close any gap 161 formed between the device 100 and an external surface of a graft. The crimping element 155 includes a tubular body 157 and an arcuate projecting member 159 extending from the tubular body. The projecting member 159 substantially conforms to the arcuate shape of the graft, thereby eliminating any gap. In addition, where a graft is to be anastomosed to a vessel having a smaller diameter, any excess graft material can be gathered at an end 163 of the projecting member 159 and pressed against an adjacent spacer element 118 or anchor element 110 to eliminate spaces or wrinkles in the graft.

In one embodiment, illustrated in FIG. 7, the tissue-penetrating protrusions 116 are of a length such that they do not extend into the lumen of the affected vessel. Instead, the tissue-penetrating protrusions 116 lodge in the healthy adventitia of the vessel, and do not affect any diseased intima having a layer of calcified plaque 162. A balloon or rigid obturator (e.g., 181 in FIG. 7D) can be inserted into the lumen of the vessel in a manner known to those of ordinary skill in the art to prevent collapse of the vessel as the device 100 is actuated. In one example, the obturator can be inserted by way of a catheter through the groin area.

Figure 7D:
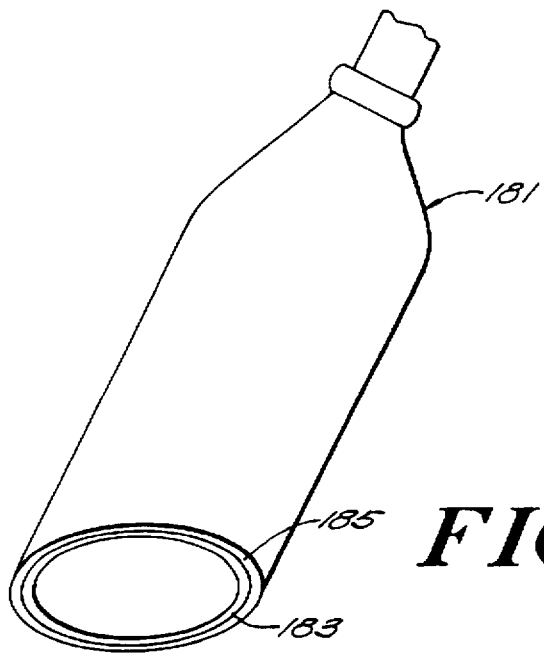
FIG. 7D is a perspective sectional view of an obturator adapted for use in conjunction with the anastomotic device of FIG. 7.

As shown in FIG. 7D, a balloon obturator 181 can include an inner layer 183 and a sheath 185 surrounding the inner layer. The sheath 185 resists penetration by the tissue-penetrating protrusions 116 and protects the inner layer 183 from puncture as the anastomotic device anastomoses one vessel to another. The sheath 185 is formed from suitable puncture resistant materials, such as latex.

Figure 8:
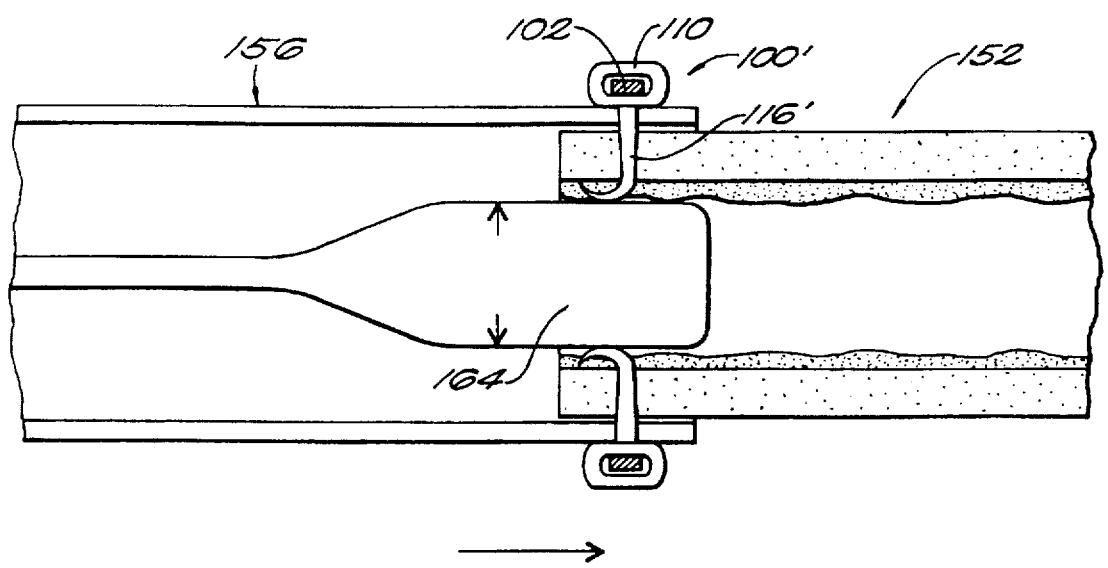
FIG. 8 is a cross sectional view of an alternative embodiment of an anastomotic device in accordance with the present invention.

In another embodiment, shown in FIG. 8, a device 100' includes tissue-penetrating protrusions 116' having a length sufficient to penetrate the intima and extend into the lumen of a vessel and into contact with a rigid obturator 164. Such contact with obturator 164 causes the tissue-penetrating protrusions 116' to deform as the device fully engages the vessel. The resulting deformed tissue-penetrating protrusions 116' can help to maintain a seal between the graft 156 and vessel 152 to prevent or minimize any leakage of blood between the vessel and the graft. This embodiment is well suited for a distal anastomosis in which the graft overlaps the end of the vessel and blood flows from the graft to the vessel.

Figure 9:
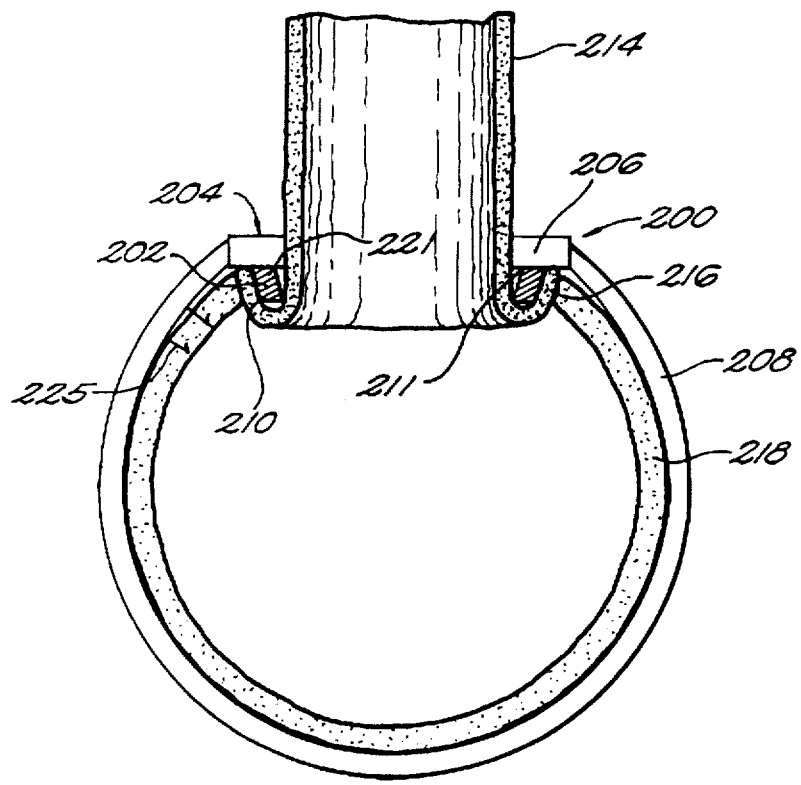
FIG. 9 is a cross sectional view of a further embodiment of an anastomotic device in accordance with the present invention.
Figure 10:
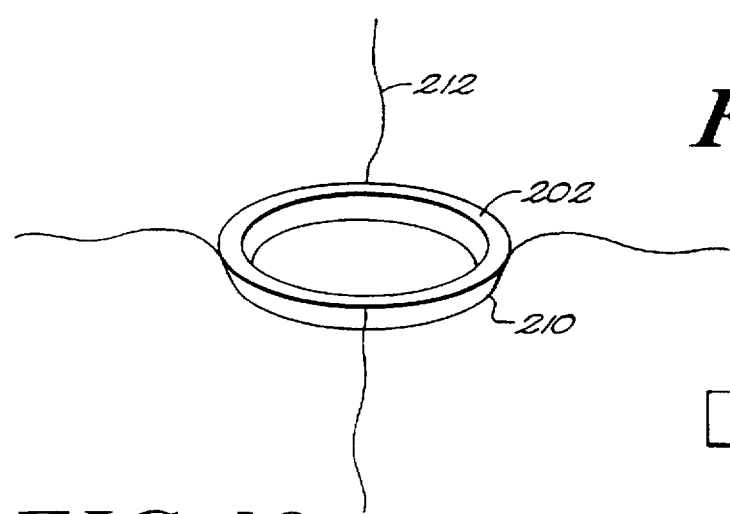
FIG. 10 is a perspective view of an anastomotic ring forming a portion of the anastomotic device of FIG. 9.
Figure 11:
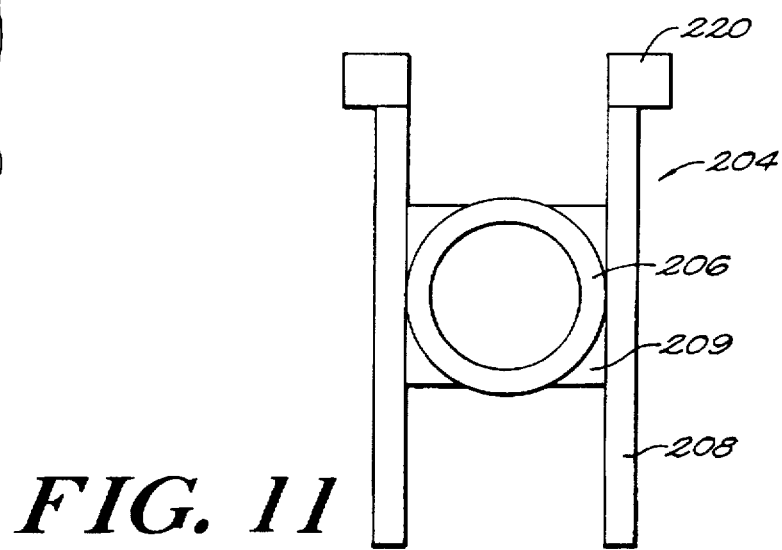
FIG. 11 is a top view of a harness assembly forming a portion of the anastomotic device of FIG. 9.

FIGS. 9-11 illustrate an anastomotic device 200 that is useful for an end-to-side anastomosis. Device 200 includes a semi-rigid anastomotic ring 202 and a harness assembly 204. The harness assembly 204 includes a semi-rigid harness ring 206 and a pair of flexible members 208 secured thereto. The harness assembly 204 can include connecting portions 209 extending laterally from the flexible members 208 to the harness ring 206. The anastomotic ring 202 includes a tapered outer surface 210 and, optionally at least one filamentary member 212 extending from the anastomotic ring 202 that can be used to secure the anastomotic ring to the harness assembly 204. The harness ring 206 includes a radially overlapping portion with respect to the anastomotic ring 202 as the inner diameter of the harness ring is less than the outer diameter of the anastomotic ring.

Figure 9A:
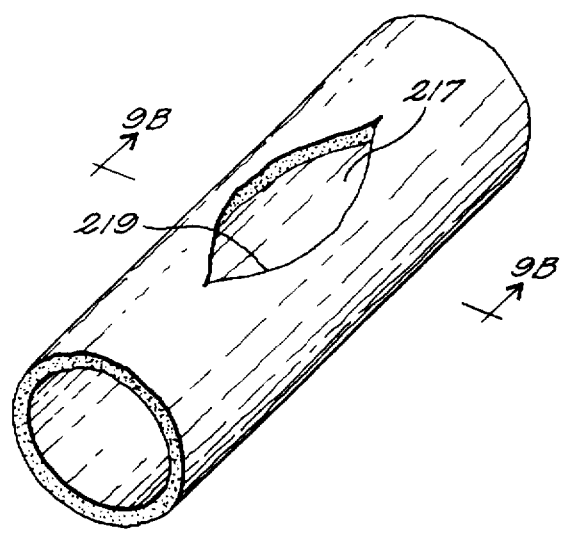
FIG. 9A is a perspective view of a prior art vessel having a hole punched therein.
Figure 9B:
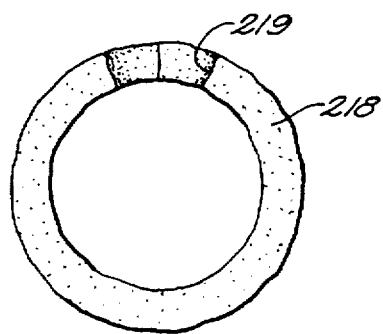
FIG. 9B is a cross sectional view of the vessel of FIG. 9A.

In operation, device 200 is used by first placing a first vessel segment 214 through the harness ring 206 and the anastomotic ring 202. A portion 216 of the first vessel segment 214 is everted over the anastomotic ring 202. A hole 217 is then cut in a second vessel 218 by means of a puncher using techniques well known to those of ordinary skill in the art (FIGS. 9A, 9B). The hole 217 has a surface 219 that is tapered inwardly from the adventitia to the intima. The hole 217 has a diameter slightly smaller than the diameter of the anastomotic ring 202.

The everted portion 216 is then placed into the hole formed in the second vessel 218. The harness assembly 204 is cinched down to the second vessel 218 by the flexible members 208 in conjunction with locking mechanisms 220. As the harness assembly 204 is secured to the second vessel, the overlapping portion of the harness ring 206 and anastomotic ring 202 retains the everted portion 216 of the first vessel in sealed engagement in the hole in the second vessel. The optional filamentary members 212 can then be used to secure the anastomotic ring to the harness assembly 204 and vessel and the connecting portions 209 cause the harness and anastomotic rings 206, 202 to conform to the annular outer surface of the second vessel 218.

For a substantially perpendicular end-to-side anastomosis of the first and second vessels 214, 218, the hole 217 and corresponding harness and anastomotic rings 206, 202 will be annular. If the first vessel 214 is to be anastomosed at an angle with respect to the second vessel 218, the formed hole 217 and corresponding rings 206, 202 will be generally oval in shape.

The anastomotic junction of the first and second vessels 214, 218 must not leak in order to achieve a successful anastomosis. The anastomotic device 200 can include additional features to assist in sealing the vessels. For example, a type of bio-sealant 211, of the type known to one of ordinary skill in the art, can be placed under and in the area of the harness ring 206 to seal the harness ring and the anastomotic ring 202 and/or first vessel. Also, the harness assembly 204 can include tissue-penetrating teeth 225, which can be barbed, to secure and seal the harness assembly and the second vessel 218.

In addition, the harness ring 206 can include a surface feature, such as a ridge, to enhance sealing engagement with a surface feature in the opposing surface of the anastomotic ring 202. Various complementary surface features on the harness assembly 204 and the anastomotic ring 202 can be also be used. A further sealing enhancement utilizes one or more surgical clips for grasping a portion of the first vessel 214, the harness ring 206, and/or the second vessel 218. In a still further embodiment, the portion of the vessel everted over the anastomotic ring 202 can extend further so as to be engaged by the harness ring. The harness and anastomotic rings 206, 202 can include one or more complementary surface features 221 that can penetrate through the everted portion of the first vessel and secure the harness and anastomotic rings together.

The sutureless anastomotic device of the present invention can be used both in an open surgery and in closed surgery, such as laparascopic surgery. Such closed surgical techniques provide significant advantages over more invasive, open surgical techniques where much larger incisions are required. The benefits of closed surgery include reduced recovery time, decreased pain or discomfort and a considerable cost savings. Another important advantage of the sutureless anastomotic device of the present invention is the reduced time required to anastomose vessels as compared with known suturing techniques. This reduction in time significantly reduces risk to the patient and increases the success rate of surgical procedures.

The exovascular device provides further advantages over sutures. The device can be anchored to healthy adventitia whereas sutures must penetrate plaque layered on the intima of the vessel, risking dislodgement of chunks of plaque.

One of ordinary skill in the art will realize further features and advantages of the invention from the above-described embodiments. Accordingly, the invention is not to be limited by what has been particularly shown and described, except as indicated by the appended claims. All references cited herein are expressly incorporated by reference in their entirety.

What is claimed is:

1. An anastomotic device, comprising:
   a flexible member having a first end and a second end and a first inner surface and a second outer surface, the flexible member being formable into a loop of an adjustable size; and
   at least one anchoring elements mounted upon the inner surface of the flexible member, each anchoring element having at least one tissue penetrating protrusion formed on one surface thereof.

2. The anastomotic device according to claim 1, wherein at least one of the anchoring elements is slidably mountable upon the flexible member.

3. The anastomotic device according to claim 1, further including a locking mechanism disposed on one of the first or second ends of the flexible member, the locking mechanism including an opening formed therein for receiving the other of the first or second ends of the flexible member.

4. The anastomotic device according to claim 3, wherein the locking mechanism is immovably affixed to the first end of flexible member.

5. The anastomotic device according to claim 3, wherein the opening of the locking mechanism includes at least one surface feature and one of the first or second surfaces of the flexible member includes a plurality of surface features, the at least one surface feature of the locking mechanism being engageable with a respective one or more of the surface features on the flexible member.

6. The anastomotic device according to claim 5, wherein the at least one surface feature of the locking mechanism and the plurality of surface features of the flexible member allow only unidirectional movement of the flexible member with respect to the locking mechanism.

7. The anastomotic device according to claim 6, wherein the surface features of the flexible member are mounted on the first surface of the flexible member, and comprise teeth-like members having a first surface ramped with respect to a longitudinal axis of the flexible member and a second surface orthogonal with respect to the longitudinal axis of the flexible member.

8. The anastomotic device according the claim 7, wherein the teeth-like surface features of the flexible member permit only unidirectional movement of the flexible member within the locking mechanism, the unidirectional movement taking place in direction to enable only a decrease in the diameter of the loop.

9. The anastomotic device according to claim 1, wherein the at least one tissue-penetrating protrusion of the anchoring member is oriented such that it projects radially inwardly on the loop.

10. The anastomotic device according to claim 1, wherein the at least one tissue-penetrating protrusion forms an acute angle with respect to a radial centerpoint of the loop.

11. The anastomotic device according to claim 1, further including at least one spacer element disposed on the flexible member between adjacent anchoring elements.

12. The anastomotic device according to claim 11, wherein the at least one spacer element is slidably mounted to the flexible member.

13. The anastomosis device according to claim 11, wherein the at least one spacer element is a tubular member having an inner, axial opening that is configured and dimensioned to receive the flexible member.

14. The anastomotic device according to claim 11, wherein the at least one spacer element is flexible.

15. The anastomotic device according to claim 1, wherein the anchoring element is a substantially tubular member having an axial opening formed therein that is configured and dimensioned to receive the flexible member.

16. An anastomotic device, comprising:
   a flexible member having a first end and a second end and first and second surfaces;
   a locking mechanism secured to at least one of the first or second ends, the locking mechanism having at least one opening therein for receiving the other of the first or second ends such that the locking mechanism facilitates the formation of a loop having an adjustable size; and
   at least one anchoring elements mounted upon the flexible member, each anchoring element having at least one tissue penetrating protrusion formed on one surface thereof.

17. An exovascular anastomotic device, comprising:
   a flexible member having first and second ends and first and second surfaces, the member having a locking mechanism formed on the first end thereof, the locking mechanism including an opening formed therein through which the second end of the flexible member is inserted to form a loop of an adjustable diameter;
   a plurality of projections formed on one of the first or second surfaces of the flexible member, the projections cooperating with the locking mechanism to permit the second end of the flexible member to move relative to the locking mechanism in one direction to effect a decrease in the diameter of the loop;
   one or more anchor members, each having a body defining an axial opening within which the flexible member is disposed to slidably mount the anchor members on the flexible member; and at least one tissue penetrating projection formed on an inwardly facing surface of each anchoring member.

18. The device according to claim 17, further comprising at least one spacer member slidably disposed on the flexible member between at least two adjacent anchoring members.

19. An anastomotic device for anastomosing an end of a first vessel to a side of a second vessel, comprising:

an anastomotic ring adapted to be disposed about an end of the first vessel;

a harness assembly including a harness ring having a radially overlapping portion with respect to the anastomotic ring;

at least one flexible member secured to the harness ring, the at least one flexible member forming a loop of adjustable size.

20. The anastomotic device according to claim 19, further including a locking mechanism mounted on the at least one flexible member.

21. The anastomotic device according to claim 19, wherein the anastomotic ring is tapered about a circumferential outer surface.

22. A method for conducting a sutureless anastomotic procedure, comprising the steps of:

providing a sutureless anastomotic device including a flexible member in the form of a loop having an adjustable diameter, at least one anchoring element having an inwardly projecting tissue penetrating member;

placing an end of a first vessel segment within the loop;

overlapping portions of the end of the first vessel segment and an end of a second vessel segment; and applying an axial force to a first end of the flexible member to reduce the diameter of the loop such that the tissue penetrating members penetrate the overlapping portions of the first and second vessels to anastomose the first and second vessel.

* * * * *